(12) United States Patent
Bian et al.

(10) Patent No.: US 10,208,104 B2
(45) Date of Patent: Feb. 19, 2019

(54) FAST AND EFFICIENT CONJUGATION METHOD BASED ON THIOUREA-CATECHOL COUPLING

(71) Applicant: The Chinese University of Hong Kong, Shatin, New Territories, Hong Kong (CN)

(72) Inventors: Liming Bian, Shatin (CN); Yang Xu, Taiwai (CN); Kongchang Wei, Fanling (CN); Pengchao Zhao, Shatin (CN)

(73) Assignee: The Chinese University of Hong Kong, Shatin, N.T., Hong Kong (CN)

( * ) Notice: Subject to any disclaimer, the term of this patent is extended or adjusted under 35 U.S.C. 154(b) by 0 days.

(21) Appl. No.: 15/362,030

(22) Filed: Nov. 28, 2016

(65) Prior Publication Data

US 2017/0204161 A1 Jul. 20, 2017

Related U.S. Application Data

(60) Provisional application No. 62/266,432, filed on Dec. 11, 2015.

(51) Int. Cl.
| | | |
|---|---|---|
| C09J 189/00 | (2006.01) |
| C08H 1/00 | (2006.01) |
| C08G 65/334 | (2006.01) |
| C08G 81/00 | (2006.01) |
| C08J 3/075 | (2006.01) |
| C08J 3/24 | (2006.01) |
| C08L 71/02 | (2006.01) |
| C07K 14/78 | (2006.01) |

(52) U.S. Cl.
CPC ............... *C07K 14/78* (2013.01); *C08H 1/00* (2013.01); *C09J 189/00* (2013.01)

(58) Field of Classification Search
None
See application file for complete search history.

(56) References Cited

U.S. PATENT DOCUMENTS

| | | | | |
|---|---|---|---|---|
| 3,457,072 A * | 7/1969 | Spangler | .................. | G03C 1/46 430/394 |
| 3,920,756 A * | 11/1975 | Tahara | .................... | C07C 37/60 502/167 |
| 2002/0193451 A1* | 12/2002 | Motonari | .................. | C09G 1/02 516/9 |
| 2012/0058641 A1* | 3/2012 | Raman | ..................... | C09G 1/02 438/692 |
| 2017/0204161 A1* | 7/2017 | Bian | ....................... | C07K 14/78 |

FOREIGN PATENT DOCUMENTS

GB    856862 A  * 12/1960  ............ B41M 5/205

* cited by examiner

*Primary Examiner* — Peter A Salamon
(74) *Attorney, Agent, or Firm* — Kilpatrick Townsend & Stockton LLP

(57) ABSTRACT

The present invention provides novel methods and compositions useful for a fast and efficient chemical conjugation method of making hetero-arm polymers based on thiourea-catechol coupling. This novel conjugation method are useful in a wide variety of applications relating to the modification, ligation, and conjugation of large or small molecules to each other as well as to solid surface, including the making of adhesive materials such as hydrogels.

12 Claims, 14 Drawing Sheets

FAST AND EFFICIENT CONJUGATION METHOD BASED ON THIOUREA-CATECHOL COUPLING

RELATED APPLICATIONS

This application claims priority to U.S. Provisional Patent Application No. 62/266,432, filed Dec. 11, 2015, the contents of which are incorporated by reference in the entirety for all purposes.

BACKGROUND OF THE INVENTION

Polymer functionalization of many substrates, including proteins, nanoparticles, solid surfaces, hydrogels, etc., are of crucial importance for their applications. For example, protein-polymer conjugates provided by polymer functionalized proteins have been widely used as therapeutics, such as PEGylated proteins. However, the existing polymer conjugating methods usually produce functionalized substrate with one single polymer chain to be conjugated to the reacting site. To conjugate two or more different individual polymer chains (to form so-called hetero-arm polymers, or star-like polymers each having a core with "arms" of different polymer chains attached to the core) to the same reacting site of substrates are challenging but powerful to make highly functionalized materials with the combined properties of the conjugated polymer chains. For example, two kinds of polymer chains could be conjugated to the same active reacting site of therapeutic proteins, with one chain to prolong the half-lives of the proteins and the other to target the diseased sites. This could potentially increase the drug efficacy significantly. No existing methods for facilely conjugation of multiple different polymer chains to one single reacting site are currently in routine use. The present invention addresses this and other related needs.

BRIEF SUMMARY OF THE INVENTION

This invention provides new methods and compositions useful for a fast and efficient chemical conjugation method, which can be applied in a wide variety of applications including the modification, ligation, and conjugation of polymers or small molecules. This method can also be used to fabricate adhesive materials such as hydrogels.

In a first aspect, the present invention provides a method of preparing a multi-compound chemical structure using a catechol-functionalized compound and a thiourea-functionalized di-compound polymer (e.g., $R_1$—NCSN—$R_2$ shown in FIG. 8). The method includes these steps: (a) oxidizing the catechol-functionalized compound (e.g., $R_3$-Cat in FIG. 8) in the presence of an oxidizing agent to form the corresponding oxidized catechol-functionalized compound; and (b) conjugating the oxidized catechol-functionalized compound with the thiourea-functionalized di-compound polymer to form a catechol-conjugated tri-compound polymer (e.g., $R_1$—NCSN—$R_2$-Cat-$R_3$ in FIG. 8). In some embodiments, the method further includes a step (c) subsequent to step (b): under oxidizing conditions, conjugating at least one thiol-functionalized compound (e.g., $R_4$—SH or $R_5$—SH in FIG. 8) to the catechol-conjugated tri-compound polymer to form a multi-compound chemical structure. In some cases, two different thiol-functionalized compounds (e.g., $R_4$—SH and $R_5$—SH in FIG. 8) are conjugated to the catechol-conjugated tri-compound polymer in step (c) to form a multi-compound chemical structure (e.g., $R_1$—NCSN—$R_2$ Cat-$R_3$—$R_4$ and $R_1$—NCSN—$R_2$-Cat-$R_3$-$R_4$—$R_5$ in FIG. 8). In some embodiments, the method further includes a step, prior to step (a), of attaching a catechol molecule to a compound to form the catechol-functionalized compound. In some embodiments, the method further includes a step, prior to step (a), of reacting a compound having an amine group with another compound having an isothiocyanate group in an amine-isothiocyanate reaction to form a thiourea-functionalized di-compound polymer.

In some embodiments, step (b) of the method described above and herein is conducted in the presence of an organic solvent or an aqueous solvent. In some embodiments, step (b) of the method described above and herein is conducted at a pH of about 1 to about 14, more preferably at a pH of about 2 to 7, or about 2 to 5, or about 2.0. In some embodiments, the oxidizing agent is selected from the group consisting of NaIO4, KIO4, NaMnO4, KMnO4, Na2Cr2O7, K2Cr2O7, CrO3, and Mushroom Tyrosinase. In some embodiments, in step (b) the ratio of oxidizing agent to catechol-functionalized compound is between 0.5 and 9999.

A general illustration of the claimed method is shown in FIG. 8, wherein $R_1$, $R_2$, $R_3$, $R_4$, and $R_5$ are independently the same or different from each other, each of $R_1$, $R_2$, $R_3$, $R_4$, and $R_5$ being independently a small molecule, a polymer, a macromolecule (such as a protein, a polynucleotide, a lipid, and the like), a nanoparticle, or a surface of solid material. Any of $R_1$, $R_2$, $R_3$, $R_4$, and $R_5$ may be a compound of naturally occurring or synthetic nature.

In a related aspect, the present invention provides various compositions that may be present during different stages of the method described above and herein. First, the present invention provides a composition comprising an oxidized catechol-functionalized compound and a thiourea-functionalized di-compound polymer (e.g., $R_1$—NCSN—$R_2$ shown in Scheme 1). Second, the present invention provides a composition comprising at least one thiol-functionalized compound (e.g., $R_4$—SH or $R_5$—SH in Scheme 1) and a catechol-conjugated tri-compound polymer (e.g., $R_1$—NCSN—$R_2$-Cat-$R_3$ in Scheme 1). In some cases, there are two different thiol-functionalized compounds (e.g., $R_4$—SH and $R_5$—SH in Scheme 1) in the composition.

In a second aspect, the present invention provides a multi-compound chemical structure produced by the method described above and herein. The multi-compound chemical structure comprises a catechol core and multiple compounds covalently linked to the catechol core. In some embodiments, the multi-compound chemical structure includes at least 3 or 4 different compounds that are covalently linked to the catechol core. In some cases, the multi-compound chemical structure has 5 different compounds (e.g., $R_1$, $R_2$, $R_3$, $R_4$, and $R_5$ as shown in Scheme 1) that are covalently linked to the catechol core. In some embodiments, each of the multiple compounds is independently a small molecule, a polymer, a macromolecule, a nanoparticle, or a surface of solid material. These compounds may be synthetic or naturally occurring. For example, the compounds may be polymers such as polyamide, polyester, gelatin, and hyaluronic acid.

In a third aspect, the present invention provides a novel method of preparing a catechol-conjugated polymer using a catechol-functionalized compound and a multi-arm crosslinker, comprising the steps of: (a) oxidizing the catechol-functionalized compound in the presence of an oxidizing agent to form the corresponding oxidized catechol-functionalized compound; and (b) conjugating the oxidized catechol-functionalized compound with the multi-arm crosslinker to form the corresponding catechol-conjugated polymer. In some embodiments the oxidizing agent is selected from the group consisting of NaIO$_4$, KIO$_4$, NaMnO$_4$, KMnO$_4$, Na$_2$Cr$_2$O$_7$, K$_2$Cr$_2$O$_7$, CrO$_3$, and Mushroom Tyrosinase.

In some embodiments, the method of preparing catechol-conjugated polymer further comprises the step of attaching catechol to a molecule to form the corresponding catechol-functionalized compound prior to step (a). In some embodiments, the method of preparing catechol-conjugated polymer further comprises conjugating catechol-functionalized compounds of different structures.

In some embodiments, the present invention provides a method of preparing a catechol-conjugated polymer further comprises conducting said step (b) conjugation in the presence of aqueous or organic solvents. In some embodiments, the solvent is water. In some embodiments, the method of preparing a catechol-conjugated polymer further comprises conducting said step (b) conjugation at a pH between 1 and 14. In some embodiments, step (b) is conducted a about a pH between 1 and 12. In some embodiments, step (b) is conducted at a about a pH between 1 and 8. In some embodiments, step (b) is conducted at a pH of about 2 to 7. In some cases, step (b) is conducted at a pH of about 2.0.

In some embodiments, the method of preparing a catechol-conjugated polymer further comprises conducting said step (b) conjugation at oxidizing agent to catechol-functionalized compound ratio between 0.5 and 9999, or 0.5 and 5999, or 0.5 and 1999, or 0.5 and 999, or 0.5 and 599, or 0.5 and 199, or 0.5 and 99, or 0.5 and 59, or 0.5 and 19, or 0.5 and 9.

In a fourth aspect, the invention provides the catechol-conjugated polymer described above comprising at least one multi-arm crosslinker and connecting a plurality of catechol-functionalized compounds. In some embodiments, the catechol-functionalized compound further comprises catechol attached to a molecule. In some embodiments, the catechol-functionalized compound further comprises catechol attached to a molecule via a linker.

In some embodiments, the molecule is a small molecule or a polymer. In some cases, the molecule is a synthetic or natural polymer. In some cases, the molecule is selected from the group consisting of polyamide, polyester, gelatin, and hyaluronic acid. In some cases, the molecule is gelatin. In some embodiments, the linker further comprises at least one sulfur atom. In some cases, the linker further comprises at least one sulfur atom that is available for participation in the attachment of the catechol-functionalized compound to the multi-arm crosslinker. In some cases, the linker further comprises at least one thiourea group. In some cases, the catechol-functionalized compound is Gel-NCSN-cat. In some cases, the catechol-functionalized compound is Gel-cat.

In some embodiments, the multi-arm crosslinker comprises a molecule having a plurality of functional moieties that permit linking to compounds. In some cases, the structural segment is poly(ethylene glycol) (PEG) wherein the molecular weight of said PEG is from 100 to 1,000,000. In some cases, the molecular weight of said PEG is from 1000 to 1,000,000. In some cases, the molecular weight of said PEG is from 1000 to 100,000. In some cases, the molecular weight of said PEG is from 1000 to 50,000. In some cases, the molecular weight of said PEG is from 1000 to 10,000. In some cases, the molecular weight of said PEG is from 1000 to 5,000. In some cases, the multi-arm crosslinker further comprises at least one functional moiety containing a sulfur atom. In some cases, the multi-arm crosslinker further comprises at least one sulfur atom that is available for participation in the attachment of the catechol-functionalized compound to the multi-arm crosslinker. In some cases, the multi-arm crosslinker further comprises at least one functional moiety containing a thiourea group. In some cases, the multi-arm crosslinker comprises at least one thiourea group for each arm. In some cases, the multi-arm crosslinker is a thiourea-functionalized 4-arm poly(ethylene glycol) crosslinker (4-Arm-PEG-NCSN). In some cases, the multi-arm crosslinker is an amino-functionalized 4-armed poly(ethylene glycol) crosslinker (4-Arm-PEG-NH$_2$).

In a fifth aspect, the invention provides exemplary hetero-arm polymer functionalized structures described above in form of catechol-conjugated polymers, such as catechol-conjugated hydrogels, which are able to recover adhesion after being sheared to failure. In some embodiments, recovery of adhesion occurs at a pH of between about 0 and about 14. In some embodiments, recovery of adhesion occurs at a pH of between about 1 and about 14. In some embodiments, recovery of adhesion occurs at a pH of between about 1 and about 12. In some embodiments, recovery of adhesion occurs at a pH of between about 1 and about 8. In some embodiments, recovery of adhesion occurs at a pH of between about 2 and about 8, e.g., about 2 to about 7, or about 2 to about 7. In some cases, recovery of adhesion occurs at a pH of about 2.0. As used herein, "about" refers to +/−10% of a reference value.

In a sixth aspect, the invention provides a composition comprising the catechol-functionalized compound described above and an oxidizing agent.

In a seventh aspect, the invention provides a composition comprising the oxidized catechol-functionalized compounds described above and one or more multi-arm crosslinkers.

In an eighth aspect, the invention provides a composition comprising a catechol molecule and the compound conjugated a linker described above.

BRIEF DESCRIPTION OF THE DRAWINGS

FIG. 1A shows the cure time (inset) and storage modulus of the Gel-cat (red) and Gel-NCSN-cat (blue) hydrogels as a function of the NaIO$_4$/catechol ratio from 0.5 to 6. (*Gel-NCSN-cat cannot form hydrogels with NaIO$_4$/catechol ratio lower than 1). FIG. 1B shows curing time (inset) and storage modulus of the Gel-cat (red) and Gel-NCSN-cat (blue) hydrogels as a function of pH from 2 to 10. (*Gel-cat cannot form hydrogels at low pH level, and the rheology data can only be obtained at pH=6 or above).

FIG. 6A shows the lap-shear adhesion strength of the Gel-cat hydrogels that are crosslinked by PEG-NCSN (pH=2.0/7.4) and PEG-NH$_2$ (pH=7.4) (n=3). Inset shows the peak adhesion stress. FIG. 6B shows the adhesion recovery of the Gel-cat hydrogels crosslinked by PEG-NCSN (pH=2.0/7.4) and PEG-NH$_2$ (pH=7.4). The recovered adhesive strength is normalized to the initial adhesive strength and presented in the form of percentage (%) (n=3).

DETAILED DESCRIPTION OF THE INVENTION

I. Definitions

Figure 1A:
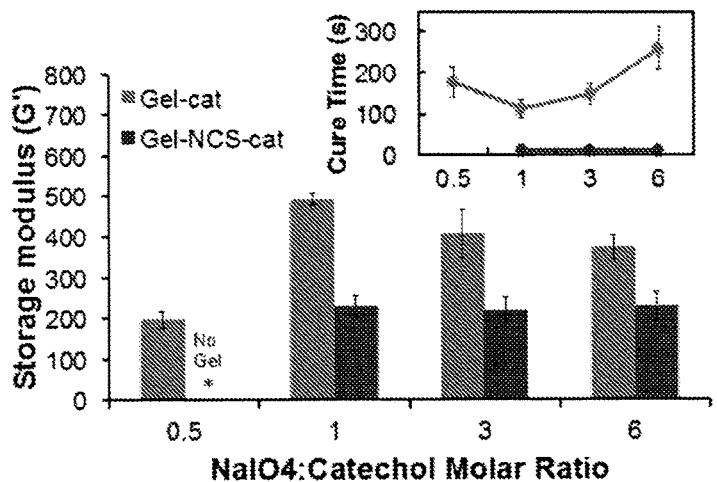
FIGS. 1A and 1B show the investigation of the gelation behavior and mechanical properties of hydrogels formed by Gel-NCSN-cat and Gel-cat.
Figure 1A:
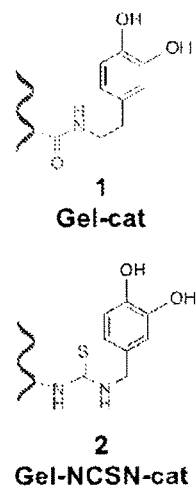

In this disclosure, the term "catechol" when used alone or in the form of "catechol-functionalized" or "catechol-conjugated," broadly encompasses all three ortho isomers of benzenediol: (1) catechol as the conventionally named compound, also known as pyrocatechol or 1,2-dihydroxybenzene; (2) resorcinol, or 1,3-dihydroxybenzene; and (3) hydroquinone, or 1,2-dihydroxybenzene. A compound may be attached to any carbon of the benzene ring not occupied by the two hydroxyl groups in order to be a "catechol-functionalized compound" or "catechol-conjugated compound." For example, the R$_3$ moiety may be linked to any one of the carbons at positions 3 to 6, preferably at position 4 or 5.

As used herein, the term "catechol-conjugated polymer" refers to a plurality of catechol-functionalized compounds conjugated by a crosslinker, such as a multi-arm crosslinker. The catechol-functionalized compounds can be the same or different structures. Examples of catechol-conjugated polymers include: hydrogels, organogels, as well as other polymer networks.

As used herein, the term "multi-arm crosslinker" refers to a molecule having a plurality of functional moieties that permit chemical conjugation of compounds including catechol-functionalized compounds. The multi-arm crosslinker can also have structural segments or "arms" that increase spatial accessibility to the attached functional moieties. For example, the multi-arm crosslinker can refer to a molecule having two-arm, three-arm, four-arm or other multi-arm structural segments attached functional moieties. Additionally, the structural segments can be poly(ethylene glycol) (PEG) having a molecular weight of from 100 to 1000000. For example, the multi-arm crosslinker can be an amino-functionalized 4-armed poly(ethylene glycol) crosslinker (4-Arm-PEG-NH$_2$). Additionally, the multi-arm crosslinker can also have functional moieties that contain sulfur atoms. The multi-arm crosslinker can also have functional moieties that include thiourea groups. The multi-arm crosslinker can also have all of the functional moieties be thiourea groups. For example, the multi-arm crosslinker can be a thiourea-functionalized 4-arm poly(ethylene glycol) crosslinker (4-Arm-PEG-NCSN).

The terms "oxidizing agent" and "oxide" as used herein encompass a broad range of compounds with the ability to oxidize other compounds, especially catechol. The term oxide includes but is not limited to metal oxides such as alkali earth and transition metal oxides. The term oxide also includes bio oxidation agents. Exemplary oxidizing agents include NaIO$_4$, KIO$_4$, NaMnO$_4$, KMnO$_4$, Na$_2$Cr$_2$O$_7$, K$_2$Cr$_2$O$_7$, CrO$_3$, and Mushroom Tyrosinase.

As used herein, the term "catechol-functionalized compound" refers a molecule attached to a catechol. The molecule can attach to catechol by a linker. The term molecule can be small molecules and macromolecules including polymers. Molecules utilized in the synthesis of catechol-functionalized compounds include, but are not limited to, synthetic and natural polymers such as polyamide; polyester; gelatin; gels; hyaluronic acid, etc. The linker can also contain sulfur atoms. The linker can also contain thiourea groups. For example, the catechol-functionalized compound can be Gel-NCSN-cat or Gel-cat.

As used herein, the term "recover adhesion after being sheared to failure" refers to the ability of a polymer to recover adhesion after being lap shear-tested to failure. Lap shear to failure can be tested on a universal testing machine with the speed of 1 mm/min under the ambient conditions. Recovery of adhesion can also be measured after being sheared to failure at an acidic pH. Polymer recovery of adhesion can range between 0 to 100%, e.g., 10 to 90%, 20 to 80%, 25 to 75%, or 30 to 50%.

II. Production of Catechol-Conjugated Polymers

A. General

This invention provides new methods and compositions useful for a fast, pH-independent, and efficient chemical conjugation method that can be applied in a wide variety of applications including the modification, ligation, and conjugation of large or small molecules. In particular, this method can be used to produce hetero-arm polymers or to fabricate adhesive materials such as hydrogels. For example, the present invention provides a novel method of preparing catechol-conjugated polymers using a catechol-functionalized compound and a multi-arm crosslinker by oxidizing the catechol-functionalized compound in the presence of an oxidizing agent to form the corresponding oxidized catechol-functionalized compound; and conjugating the oxidized catechol-functionalized compound with the multi-arm crosslinker to form the corresponding catechol-conjugated polymer. Additionally, the incorporation of sulfur atoms as well as thiourea groups to the multi-arm crosslinker and/or the catechol-functionalized compound results in the enhanced stability of the catechols against oxidation in the catechol-conjugated polymers leading to significant improvement in adhesion. The catechol-functionalized compounds can be the same or different structures.

Moreover, the present invention provides methods for the preparation of novel hydrogel adhesives. For example, thiourea functionalized polymers can be employed to mimic the function of mfp-6 for the preparation of adhesive hydrogels. Unlike the naturally existing nucleophiles such as cysteines (pKa=8-9) that usually react under the basic conditions,[13,18] thiourea (pKa=−1)[19] derivatives are known to be reactive toward catechol derivatives under the acidic condition due to the low pKa value.[20] The thiourea groups act as excellent nucleophile to form crosslinking with catechol-conjugated structures under acidic conditions, leading to the rapid formation of hydrogels. Due to the high reducing power of thiourea, the stability of the catechols is significantly enhanced against oxidation in the resultant hydrogel adhesives, thus leading to the significant improvement of adhesion.

B. Components and Preparation of Catechol-Functionalized Compounds

The catechol-functionalized compounds of this invention include a molecule attached to catechol via a linker. Catechol-functionalized compounds can be synthesized by attaching a catechol molecule to a compound via a linker.

The molecules utilized in the synthesis of catechol-functionalized compounds include, but are not limited to, polyamide, polyester, gelatin, and hyaluronic acid. In some embodiments, gelatin, a mixture of collagen-derived polypeptides, is chosen as the molecule used in the synthesis of catechol-functionalized compounds. In some embodiments hydrogels are chosen as the molecule used in the synthesis of catechol-functionalized compounds.

Hydrogels are a network or scaffolding of natural or synthetic polymer chains that are hydrophilic, sometimes found as a colloidal gel in which water is the dispersion medium. Being polymer networks that have high water-absorbing capacity, hydrogels often closely mimic native extracellular matrices. Hydrogels also tend to possess a degree of flexibility very similar to natural tissues, due to the relatively high water content: in some cases, hydrogels can contain well over 90% water. Common ingredients used in hydrogels include polyvinyl alcohol, sodium polyacrylate, acrylate polymers and copolymers with an abundance of hydrophilic groups. Natural hydrogel materials are being investigated for tissue engineering; these materials include agarose, methylcellulose, hyaluronan, and other naturally derived polymers. Exemplary hydrogels can be found in U.S. Pat. Nos. 8,329,763; 8,008,476; 6,534,083; 4,438,258; U.S. Patent Appl. Nos. 2013/0,034,592; 2013/0,022,569; 2002/0,009,591; and International Patent Publication Nos. WO/2001/049240; and WO/1997/030092.

Figure 8:
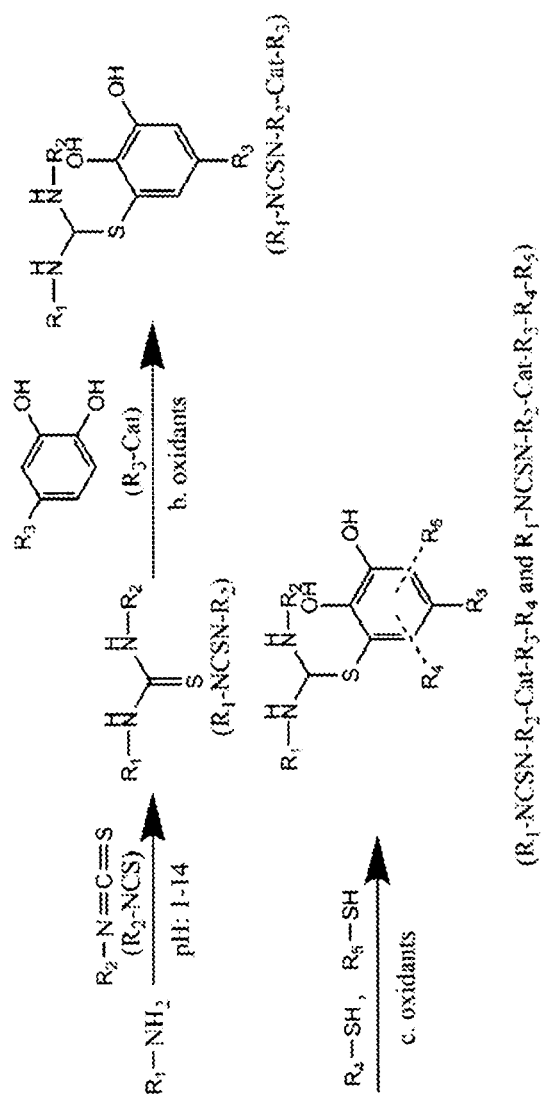
FIG. 8 shows the general procedure of preparing hetero-arm polymer-functionalized structures.

Catechol-functionalized compounds can be synthesized in several ways, including reacting catechol containing molecules with the amine-containing compounds through conventional carbodiimide coupling [1,21] or isothiocyanate-amine coupling. For example, catechol- functionalized compounds can be synthesized by reacting the amine group ($-NH_2$) with isothiocyanate group ($-N=C=S$) under basic conditions at room temperature, resulting in the isothiourea group ($-NH-C(=S)-NH-$, or $-NCSN-$) (see FIG. 8). Under oxidative conditions (sodium periodate, equal molar ratio to the catechol group), the catechol group reacts quickly with the $-NCSN-$ group under a broad pH range.

C. Components and Preparation of Multi-Arm Crosslinkers

The invention utilizes multi-arm crosslinkers having a plurality of structural segments (or arms) attached to functional moieties. In some embodiments the multi-arm crosslinker refers to two-arm, three-arm, four-arm or other multi-arm derivative. In some cases, the structural segments can have a branched or linear architecture including one or more poly(ethylene glycol) (PEG) chain wherein the molecular weight of said PEG is from 100 to 1000000. In some cases, the multi-arm crosslinker can have functional moieties containing sulfur atoms. In some cases, the multi-arm crosslinker can have thiourea groups. In some cases, the multi-arm crosslinker can have a thiourea group for each arm. The multi-arm crosslinker can be a thiourea-functionalized 4-arm poly(ethylene glycol) crosslinker (4-arm-PEG-NCSN). Additionally, the multi-arm crosslinker can be a amino-functionalized 4-armed poly(ethylene glycol) crosslinker (4-arm-PEG-$NH_2$).

Some of the multi-arm crosslinkers utilized in the present invention including two-arm, three-arm, four-arm, six-arm, and eight-arm are commercially available, e.g., Sigma-Aldrich. Additionally, multi-arm crosslinkers utilized in the present invention can be synthesized in several ways, including by further functionalizing commercially available multi-arm crosslinkers to include sulfur atoms or thiourea groups via isothiocyanate-amine coupling. For example, reacting 4-armed poly(ethylene glycol)-$NH_2$ HCl with methyl isothiocyanate and triethylamine affords the corresponding thiourea functionalized 4-arm crosslinker.

D. Components and Preparation of Catechol-Conjugated Polymers

The present invention provides a novel method of preparing catechol-conjugated polymers. A catechol-functionalized compound is polymerized with a multi-arm crosslinker by oxidizing the catechol-functionalized compound in the presence of an oxidizing agent to form an oxidized catechol-functionalized compound. Then the oxidized catechol-functionalized compound is conjugated with a multi-arm crosslinker to form the corresponding catechol-conjugated polymer. The catechol-functionalized compounds can be the same or different structures. Additionally, the incorporation of sulfur atoms as well as thiourea groups to the multi-arm crosslinker and/or the catechol-functionalized compound results in the enhanced stability of the catechols against oxidation in the catechol-conjugated polymers leading to significant improvement in adhesion.

Catechol-conjugated polymers can be synthesized by oxidizing the catechol-functionalized compounds to afford the corresponding quinone oxidized catechol-functionalized compounds followed by introduction of the multi-arm crosslinker to yield the desired catechol-conjugated polymers. For example, oxidation of Gel-cat affords the corresponding Gel-quinone, which upon addition of 4-arm-PEG-NCSN yields Catechol-conjugated polymer Gel-cat+PEG-NCSN. More specifically, catechol-conjugated hydrogels can be formed by the crosslinking of Gel-cat with 4% PEG-NCSN/PEG-NH$_2$ at targeted pH values with a NaIO$_4$:NCSN ratio of 1:1.

Figure 9:
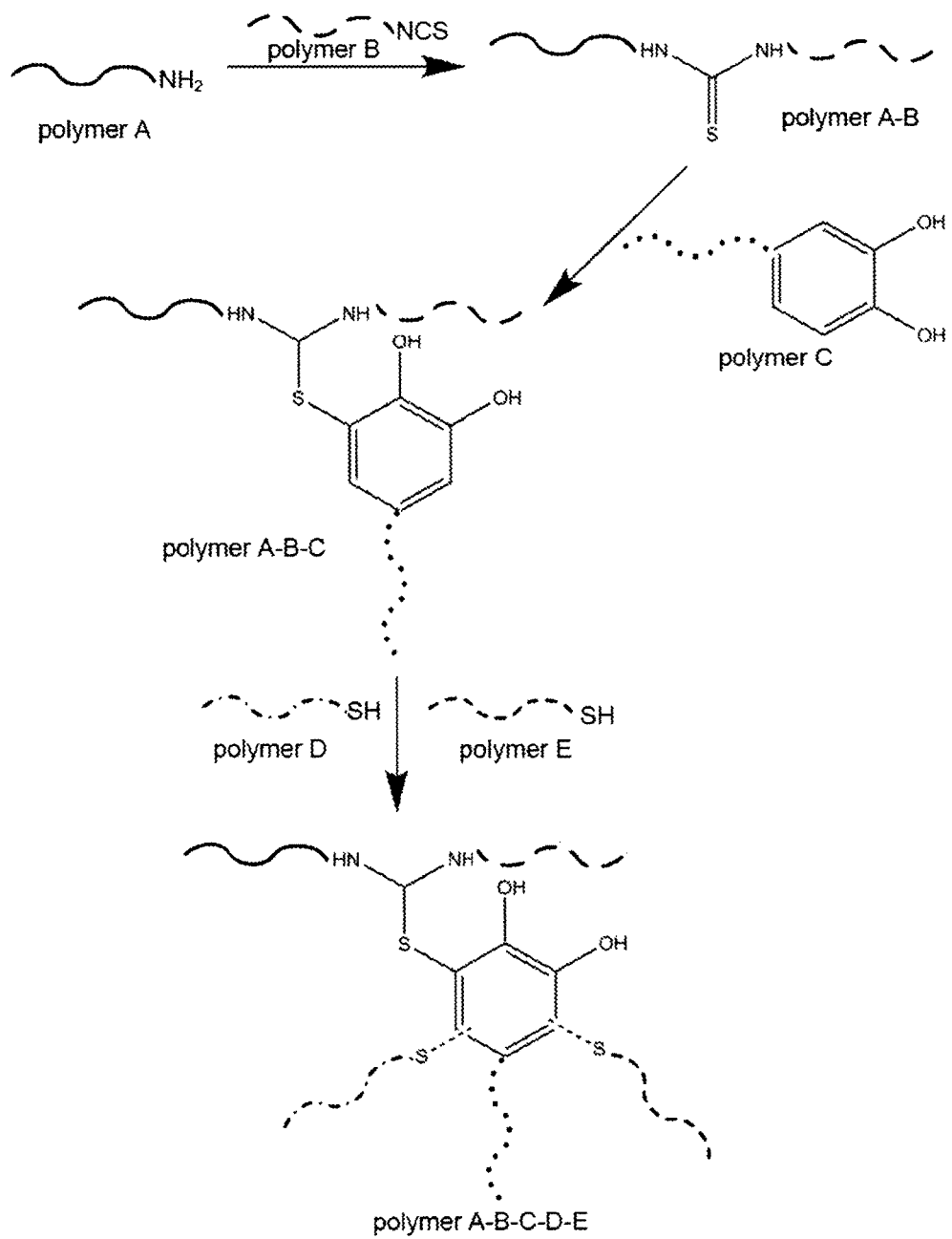
FIG. 9 shows how synthetic hetero-arm polymers can be synthesized facially by the sequential single-site coupling reactions. For example, the coupling between amine end-functionalized polymers (polymer A) with isothiocyanate end-functionalized polymers (polymer B) yields the polymer conjugate (polymer A-B), with the isothiourea in the coupling site. The catechol end-functionalized polymer (polymer C) then can be coupled to the isothiourea group under oxidative conditions, giving the hetero-arm polymers (polymer A-B-C). Thiol-functionalized polymers (polymer D and polymer E) can be furtherly conjugated to the hetero-arm polymers under oxidizing conditions to yield more complex structure such as polymer A-B-C-D-E.

Moreover, the present invention provides for the preparation of hetero-arm polymers. A hetero-arm polymer, also referred to as a "multi-compound chemical structure" in this disclosure, has a core structure and different compounds (e.g., polymer chains) attached to and extending from the core. These different compounds (in some cases polymer chains) are called "hetero arms" because for each hetero-arm polymer there are at least two, possibly three, four, five, or more chains, among which at least some are different from each other, although some others may be the same. For example, synthetic hetero-arm polymers can be synthesized facially by the sequential single-site coupling reactions. For example, the coupling between amine end-functionalized polymers (polymer A) with isothiocyanate end-functionalized polymers (polymer B) yields the polymer conjugate (polymer A-B), with the isothiourea in the coupling site. The catechol end-functionalized polymer (polymer C) then can be coupled to the isothiourea group under oxidative conditions, giving the hetero-arm polymers (polymer A-B-C). Thiol-functionalized polymers (polymer D and polymer E) can be furtherly conjugated to the hetero-arm polymers under oxidizing conditions to yield more complex structure such as polymer A-B-C-D-E (see FIG. 9).

Figure 10:
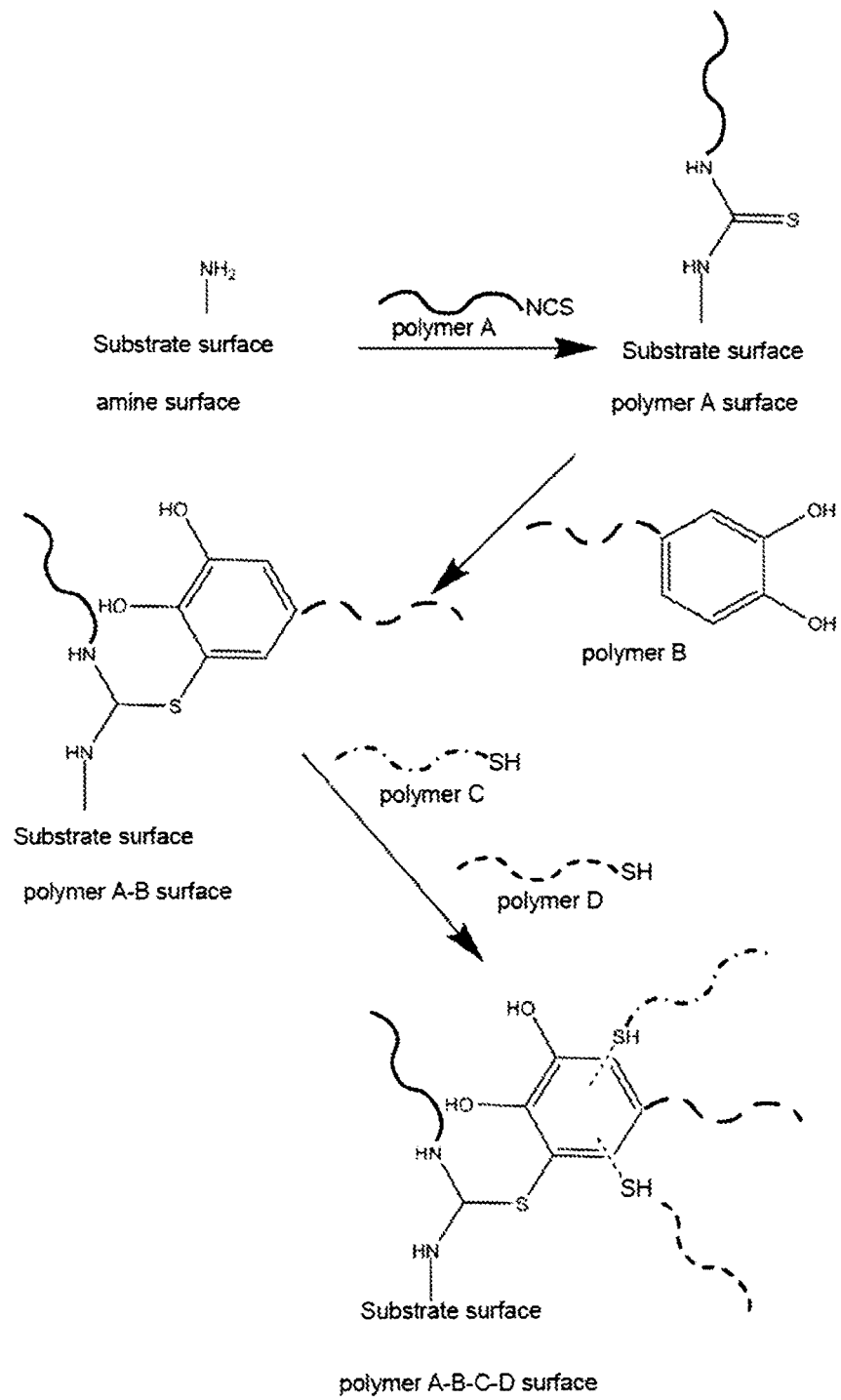
FIG. 10 shows how substrate surfaces with amines can be functionalized by hetero-arm polymers. For example, isothiocyanate end-functionalized polymers (polymer A) can be coupled to the surface amines, giving the isothiourea groups for the coupling of catechol end-functionalized polymer B. Thiol-functionalized polymers (polymer C and polymer D) can be furtherly conjugated to the hetero-arm polymers under oxidizing conditions to yield more complex hetero-arm polymer structures such as polymer A-B-C-D on the surface.

The present invention also provides for the well-defined functionalization of surface amines with hetero-arm polymers. Substrate surfaces with amines can be functionalized by hetero-arm polymers. For example, isothiocyanate end-functionalized polymers (polymer A) can be coupled to the surface amines, giving the isothiourea groups for the coupling of catechol end-functionalized polymer B. Thiol-functionalized polymers (polymer C and polymer D) can be furtherly conjugated to the hetero-arm polymers under oxidizing conditions to yield more complex hetero-arm polymer structures such as polymer A-B-C-D on the surface (see FIG. 10).

Figure 11:
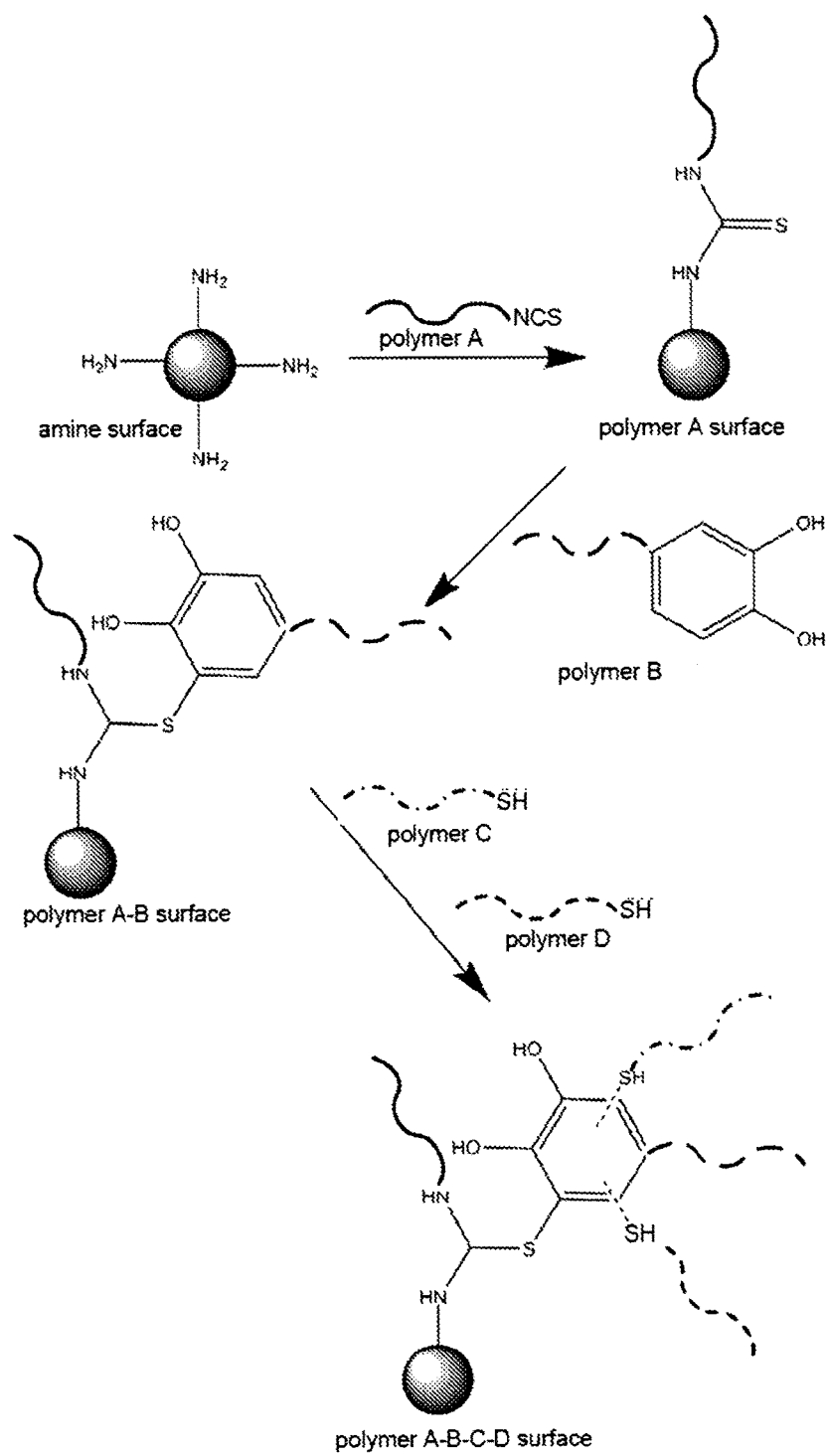
FIG. 11 shows how particle surfaces with amines can be functionalized by hetero-arm polymers. For example, isothiocyanate end-functionalized polymers (polymer A) can be coupled to the surface amines, giving the isothiourea groups for the coupling of catechol end-functionalized polymer B. Thiol-functionalized polymers (polymer C and polymer D) can be furtherly conjugated to the hetero-arm polymers under oxidizing conditions to yield more complex structure such as polymer A-B-C-D on the nanoparticle surface.

The present invention also provides for the well-defined functionalization of nanoparticles with hetero-arm polymers. Particle surfaces with amines can be functionalized by hetero-arm polymers. For example, isothiocyanate end-functionalized polymers (polymer A) can be coupled to the surface amines, giving the isothiourea groups for the coupling of catechol end-functionalized polymer B. Thiol-functionalized polymers (polymer C and polymer D) can be furtherly conjugated to the hetero-arm polymers under oxidizing conditions to yield more complex structure such as polymer A-B-C-D on the nanoparticle surface (see FIG. 11).

Figure 12:
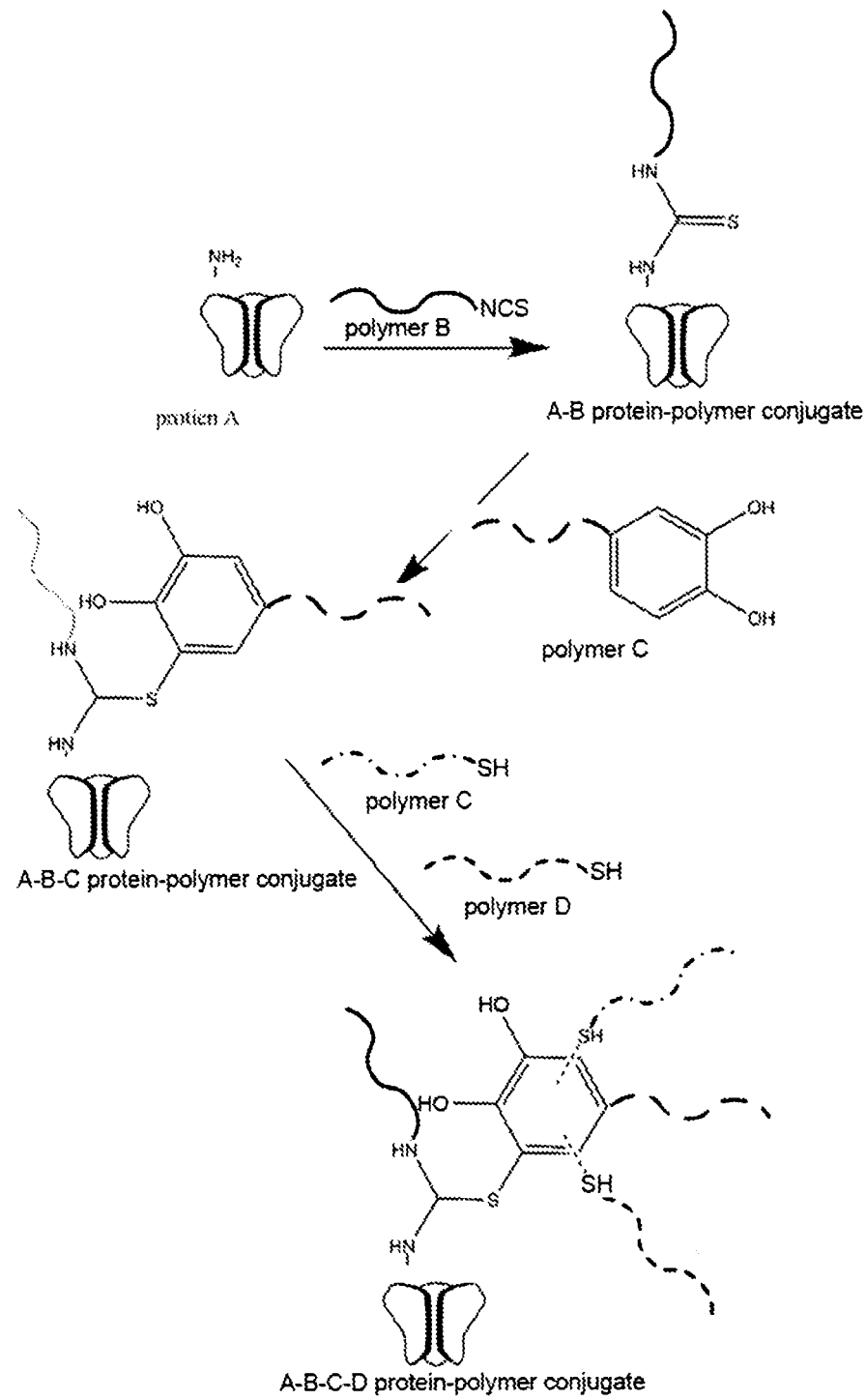
FIG. 12 shows how amines on protein surface can be functionalized by hetero-arm polymers. For example, isothiocyanate end-functionalized polymers (polymer B) can be coupled to the surface amines of the protein (A), giving the isothiourea groups for the coupling of catechol end-functionalized polymer C, yielding protein-polymer conjugate A-B-C. Thiol-functionalized polymers (polymer D and polymer E) can be furtherly conjugated to the hetero-arm polymers under oxidizing conditions to yield more complex structure such as protein-polymer conjugate A-B-C-D-E.

The present invention also provides for the sequential conjugation of different polymers to the same amine of proteins. Amines on protein surface can be functionalized by hetero-arm polymers. For example, isothiocyanate end-functionalized polymers (polymer B) can be coupled to the surface amines of the protein (A), giving the isothiourea groups for the coupling of catechol end-functionalized polymer C, yielding protein-polymer conjugate A-B-C. Thiol-functionalized polymers (polymer D and polymer E) can be furtherly conjugated to the hetero-arm polymers under oxidizing conditions to yield more complex structure such as protein-polymer conjugate A-B-C-D-E (see FIG. 12).

Figure 13:
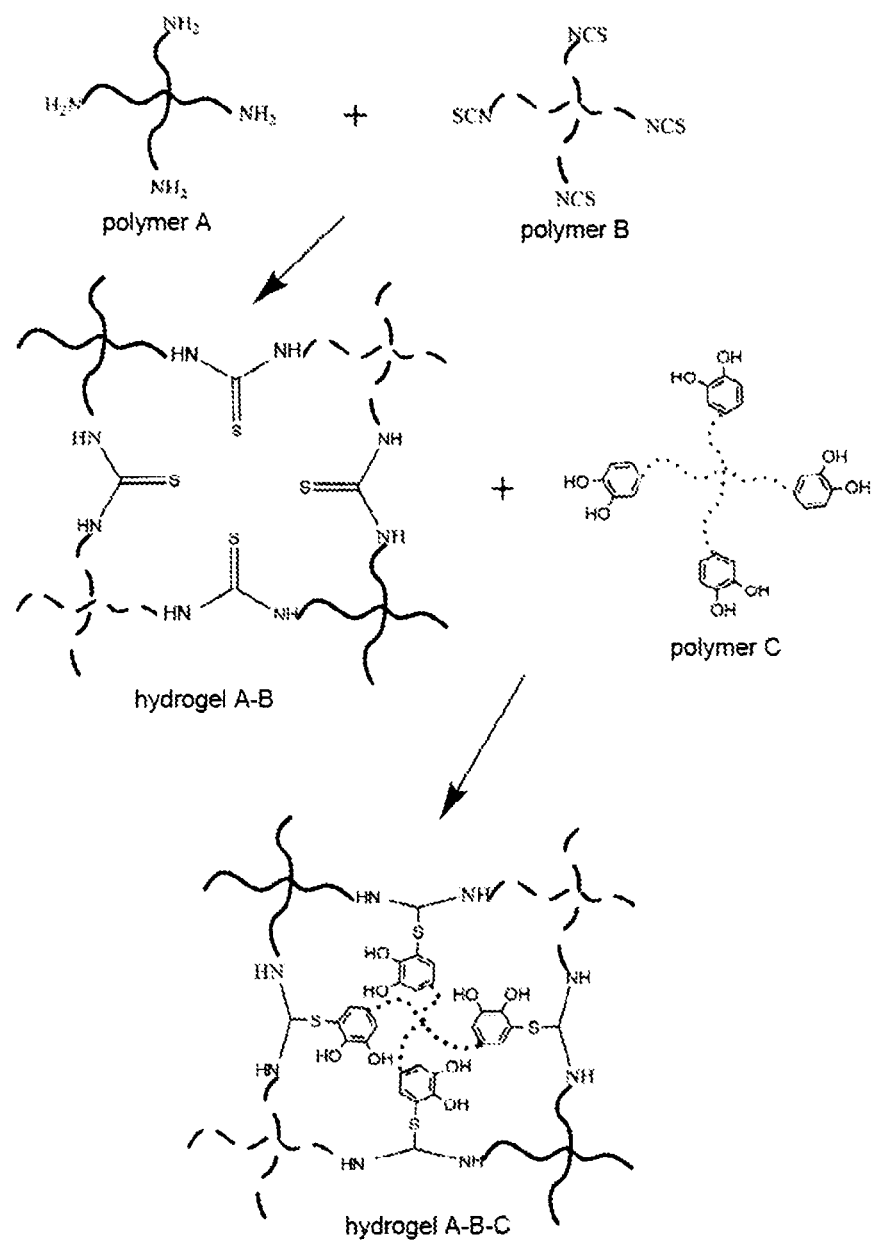
FIG. 13 shows the sequential crosslinking of hydrogel networks with identical crosslinking sites. For example, amine functionalized 4-arm polymer (polymer A) can form hydrogels with isothiocyanate functionalized 4-arm polymer (polymer B), leaving isothiourea groups at the crosslinking sites. Catechol functionalized 4-arm polymer (polymer C) can then further crosslink the polymer network at the same crosslinking sites by the coupling between isothiourea groups and catechol groups.

The present invention also provides for the sequential crosslinking of hydrogel networks with identical crosslinking sites. For example, amine functionalized 4-arm polymer (polymer A) can form hydrogels with isothiocyanate functionalized 4-arm polymer (polymer B), leaving isothiourea groups at the crosslinking sites. Catechol functionalized 4-arm polymer (polymer C) can then further crosslink the polymer network at the same crosslinking sites by the coupling between isothiourea groups and catechol groups (see FIG. 13).

Figure 14:
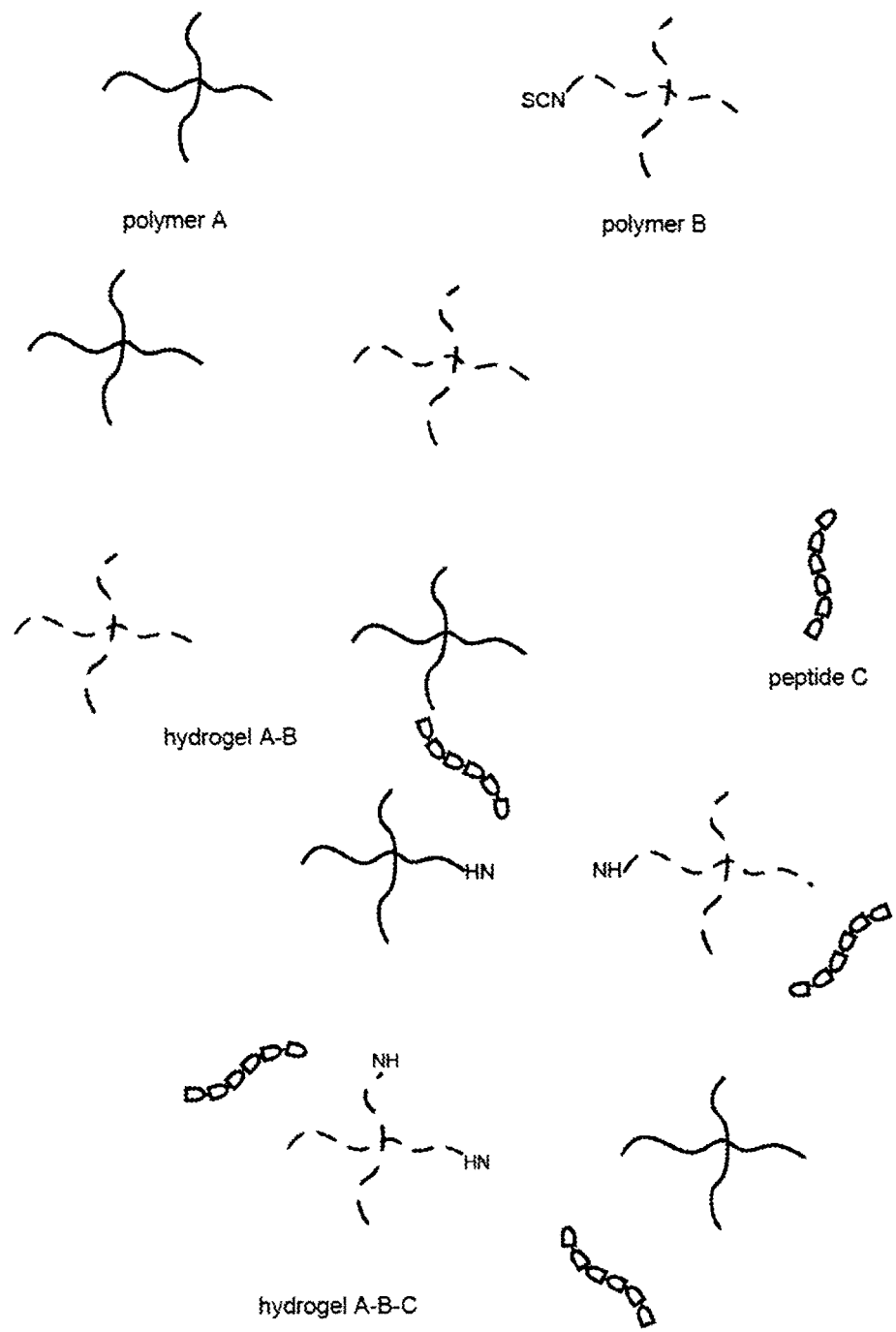
FIG. 14 shows the functionalization of hydrogels at the crosslinking sites. For example, amine functionalized 4-arm polymer (polymer A) can form hydrogels with isothiocyanate functionalized 4-arm polymer (polymer B), leaving isothiourea groups at the crosslinking sites. Catechol functionalized peptides (peptide C) can then be conjugated to the polymer network at the same crosslinking sites by the coupling between isothiourea groups and catechol groups.

The present invention also provides for the functionalization of hydrogels at the crosslinking sites. For example, amine functionalized 4-arm polymer (polymer A) can form hydrogels with isothiocyanate functionalized 4-arm polymer (polymer B), leaving isothiourea groups at the crosslinking sites. Catechol functionalized peptides (peptide C) can then be conjugated to the polymer network at the same crosslinking sites by the coupling between isothiourea groups and catechol groups (see FIG. 14).

III. Measurement of Adhesiveness

In order to measure recovery of adhesion after being sheared to failure, catechol-conjugated polymers can be lap shear-tested to failure then observe and measure any recovery of adhesion. Catechol-conjugated polymers can also recover adhesion after being sheared to failure at an acidic pH. Catechol-conjugated polymer recovery of adhesion can range from 0 to 100%. Catechol-conjugated polymer recovery of adhesion can be as high 100%. Moreover, catechol-conjugated polymers can recover some adhesion after being sheared to failure multiple times. Catechol-conjugated polymers can also recover some adhesion after being sheared to failure five times.

EXAMPLES

The following examples are provided by way of illustration only and not by way of limitation. Those of skill in the art will readily recognize a variety of non-critical parameters that could be changed or modified to yield essentially the same or similar results.

Example 1

Preparation and Characterization of Gel-cat Polymer as a Catechol-functionalized Compound Mussel foot proteins (mfps), including mfp-1, mfp-3 and mfp-5, are known as excellent natural adhesives in mussel feet. The catechol side chain of L-3,4-dihydroxyphenylalanine (L-DOPA) is the key component of these proteins that enables mussels to tightly attach to various surfaces.

Inspired by these L-DOPA containing proteins, many functional polymers bearing L-DOPA-like structures have recently been synthesized to mimic such natural adhesives. Generally, synthetic polymers functionalized with DOPA or its catechol analogues (e.g., dopamine), can be crosslinked to form adhesive hydrogels by oxidation.[1-4] It has been proposed that the oxidant-induced polymerization of the catechol at basic pH is responsible for the hydrogel formation. Specifically, catechol is firstly oxidized to quinone. This intermediate product subsequently induces the aryloxy radical-mediated phenol coupling,[2,3] leading to the polymer crosslinking and the hydrogel formation. However, such quinone-mediated crosslinking inevitably reduce the adhesiveness owing to the loss of catechol structure.[5,6] Previous studies have shown that the quinone formation under basic conditions diminishes the adhesion of the catechol-functionalized hydrogels to mica,[7-9] titania[10] and titania oxide surfaces.[6,11,12] Therefore, to better preserve the adhesiveness, the catechol structure should be protected from oxidation, and this is intrinsically contradictive to the crosslinking condition of the mfp-mimicking polymers.[1-3]

In nature, mussels overcome the adverse effects of catehol oxidation by adopting thiol-rich mfp-6 as a reducing agent with an unusual low $pK_a$ ($pK_a$=3-4)[13,14] The thiolates of mfp-6 can reduce the quinones[6,13-15] to the original catechol structures at acidic pH (pH≤5)[7,13,16], thus restoring and even enhancing the adhesion to substrates.[13,16,17] Besides being an natural antioxidant,[13,14,17] it is worth noting that mfp-6 is also crucial for improving cohesion among the plaque proteins.[13,15] In light of that, an "artificial mfp-6" can be employed in the structural design of the polymeric hydrogel adhesives. The "artificial mfp-6" should possess three key properties: (i) having a low $pK_a$ so that the crosslinking can be performed at acidic pH (pH≤5), (ii) being capable of reducing the quinone back to catechol (for better adhesion), and (iii) containing strong nucleophiles (such as thiols) so that it can efficiently interact with quinone to crosslink the polymeric network of the hydrogels (for better cohesion).

Gelatin, a mixture of collagen-derived polypeptides, was chosen as the polymer backbone. To mimic the DOPA-rich mfps (mfp-1, mfp-3 and mfp-5), catechol-functionalized gelatin was synthesized by conventional carbodiimide coupling[1,21]. The cardodiimide coupling yields amide-linked catechol-functionalized gelatin polymers, termed Gel-cat, (1, FIG. 1A).[21] Consistent with the previous reports, Gel-cat can be crosslinked by oxidation only under basic conditions. The catechol content of gelatin is estimated by the $^1$H NMR and UV-vis measurements. To control the amount of catechol groups present in the two different polymers, 10% Gel-cat is used to prepare the control hydrogels whereas 4% of Gel-NCSN-cat is used to prepare hydrogels for comparison throughout the whole study, unless otherwise specified. Hydrogels were formed by the crosslinking of catechols at different oxidant content. Firstly, Gel-cat were dissolved in PBS, the concentration of Gel-cat were 100 mg/mL, in order to set an equal molar amount of catechol. Then, the $NaIO_4$ was added and kept at a molar ratio of 0.5-6 relative to the catechol/pH levels from pH=6 to pH=10. The mixtures were immediately vortexed and the gelation time was determined when the polymer solution ceased flowing after inverting the vials.

Example 2

Preparation and Characterization of 4 Gel-NCSN-cat Polymer as A Catechol-functionalized Compound To mimic the DOPA-rich mfps (mfp-1, mfp-3 and mfp-5), catechol-functionalized gelatin was synthesized by isothiocyanate-amine coupling. Dopamine-isothiocyanate[22,23], was first synthesized which was then grafted to the gelatin compound via isothiocyanate-amine coupling, thereby producing the catechol-functionalized compound Gel-NCSN-cat (2, FIG. 1A). The thiourea linker of Gel-NCSN-cat mimics the reducing thiols of mfp-6. The catechol content of gelatin is estimated by the $^1$H NMR and UV-vis measurements. Hydrogels were formed by the crosslinking of catechols at different oxidant content. Firstly, the Gel-NCSN-cat and Gel-cat were dissolved in PBS, the concentration of Gel-NCSN-cat and Gel-cat were 40 mg/mL and 100 mg/mL, respectively, in order to set an equal molar amount of catechol. Then, the $NaIO_4$ was added and kept at a molar ratio of 1-6 relative to the catechol/pH levels from pH=2 to pH=10. The mixtures were immediately vortexed and the gelation time was determined when the polymer solution ceased flowing after inverting the vials.

Example 3

Preparation and Characterization of 4-armed-Peg-NCSN—$CH_3$ 4-armed poly(ethylene glycol)-$NH_2$ HCl sat was dissolved in dry DCM. Methyl isothiocyanate and triethylamine were added in the solution. The mixture was poured into cold diethylether and the PEG product was obtained by centrifuge and vacuum dry. The graft ratio of methyl isothiocyanate was determined by the integration of relevant peaks in the $^1$H NMR spectrum.

Example 4

Preparation of Hydrogel (Gel-NCSN-cat and Gel-cat) at Different $NaIO_4$: Catechol Ratios Hydrogels were formed by the crosslinking of catechols at different oxidant content. Firstly, the Gel-NCSN-cat and Gel-cat were dissolved in PBS. Then, the $NaIO_4$ was added and kept at a molar ratio of 0.5-6 relative to the catechol. The mixtures were immediately vortexed and the gelation time was determined when the polymer solution ceased flowing after inverting the vials.

Example 5

Preparation of Hydrogel (Gel-NCSN-cat and Gel-cat) at Different pH Values

Hydrogels were formed by crosslinking catechols at different pH conditions. Firstly, the Gel-NCSN-cat and Gel-cat were dissolved in pH buffers (2, HCl; 4, MES; 6, PBS; 7.4, PBS; 8.5, PBS; 10, NaOH). The $NaIO_4$ was then added at a molar ratio of 1.0 relative to the catechol. The mixtures were immediately vortexed because of their short curing time, and the gelation time was determined when the polymer solution ceased flowing after inverting the vials.

Example 6

Preparation and Characterization of Catechol-Conjugated Polymers

To investigate the contribution of the thiourea linkage to the Gel-NCSN-cat gelation, thiourea-functionalized 4-arm poly(ethylene glycol) crosslinkers (PEG-NCSN) to crosslink the Gel-cat under oxidized conditions were synthesized.

As expected, the gelation is fast (within 1 min) under all tested pH values. However, the negative control with the addition of amino-functionalized 4-armed poly(ethylene glycol) (PEG-NH$_2$) only formed hydrogels with Gel-cat at higher pH levels (pH≥6) with significantly longer curing time. Such difference can be attributed to the lower pK$_a$ of thiourea compared to that of the amino group and also indicates that thiourea is a highly effective nucleophile for coupling with the oxidized catechol (quinone).

Figure 1B:
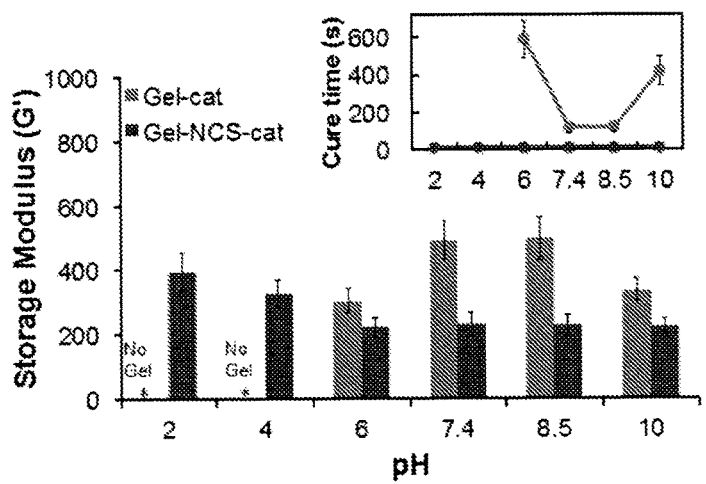

The gelation time of Gel-cat demonstrates a strong dependency on both the oxidant content (molar ratio between NaIO$_4$ and catechol) and pH value (red curves in FIGS. 1A and 1B). These observations are in agreement with the previously reports[2,3,24] that both oxidant content and pH are responsible for the stoichiometric ratio between the reduced (catechol) and oxidized (quinone) form of catechol. It is worth noting that an optimal ratio between the catechol and quinone is needed for rapid gelation in such case. In sharp contrast, the gelation time of Gel-NCSN-cat shows no obvious dependency on either the oxidant content or the pH value. Regardless of the oxidant content and pH, extremely rapid gelation (cure time≤3 s) can be achieved for the Gel-NCSN-cat (See blue curves in FIGS. 1A and 1B). Besides, dynamic rheological studies reveal that the mechanical properties of the resultant hydrogels show similar dependency on the gelation condition. Specifically, the storage modulus of Gel-cat hydrogels shows an initial increase and subsequent slight decrease with increasing oxidant contents or pH values (red bars in FIGS. 1A and 1B), supporting the notion that an optimal oxidant content and pH value can give rise to the faster and denser crosslinking of hydrogel networks composed of polymers functionalized with catechols via the amide link.[2,3] In contrast, the storage modulus of the Gel-NCSN-cat hydrogels shows negligible dependency on oxidant content and pH values (blue bars in FIGS. 1A and 1B). Interestingly, the Gel-NCSN-cat can form much stronger hydrogels even under acidic conditions (pH=2, pH=4) that impede the gelation of the Gel-cat. This remarkable difference in the gelation behavior and mechanical properties of the resulting hydrogels possibly indicate two distinct crosslinking mechanisms for the two catechol-conjugated polymers. Given the same gelatin backbone, such significant difference between the Gel-cat and Gel-NCSN-cat hydrogels is likely attributed to the different linkage between the gelatin backbone and the catechol group.

Example 7

Mechanism of Catechol-Conjugated Polymers

Figure 3:
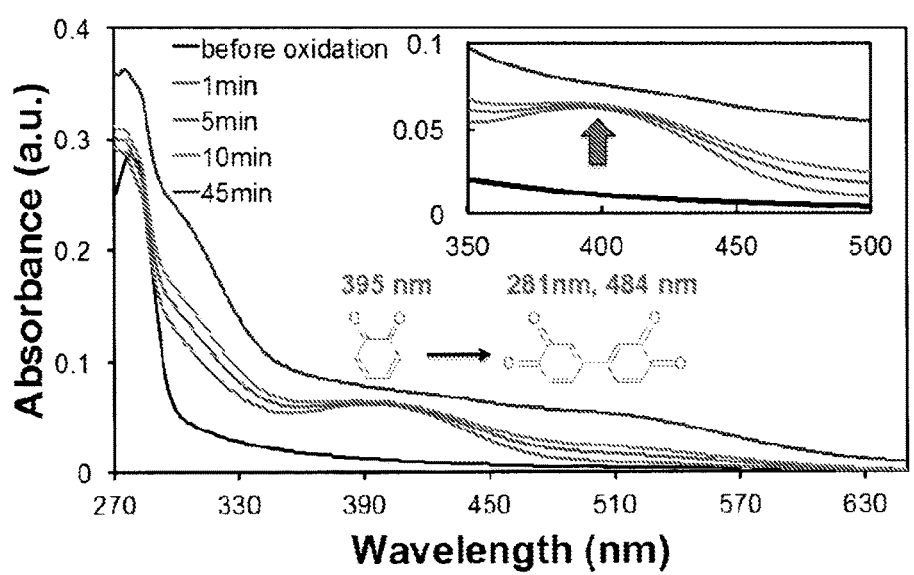
FIG. 3 shows UV-vis spectra for oxidation (NaIO$_4$:cat=1:1, pH=6.0) of Gel-cat. Solutions were scanned immediately after the addition of NaIO$_4$. The arrows indicate the progression of the spectra with time.
Figure 4:
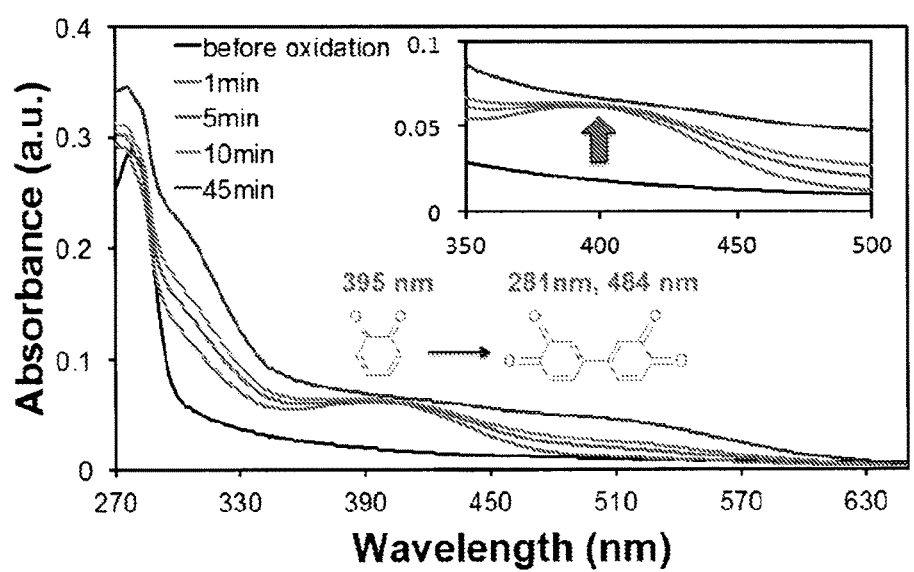
FIG. 4 shows UV-vis spectra for oxidation (NaIO$_4$:cat=1:1, pH=6.0) of Gel-cat and PEG-NH$_2$. Solutions were scanned immediately after the addition of NaIO$_4$. The arrows indicate the progression of the spectra with time.
Figure 5:
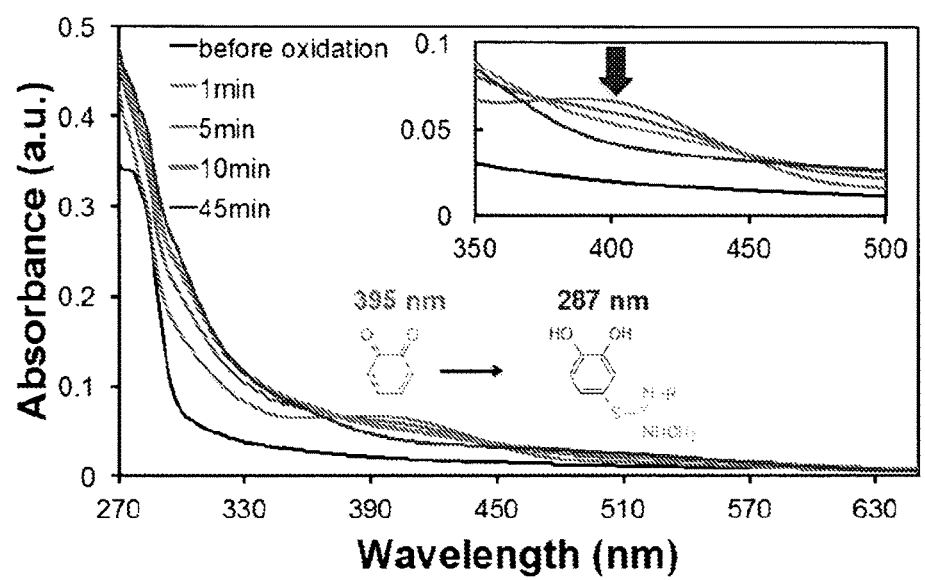
FIG. 5 shows UV-vis spectra for oxidation (NaIO$_4$:cat=1:1, pH=6.0) of Gel-cat and PEG-NCSN. Solutions were scanned immediately after the addition of NaIO$_4$. The arrows indicate the progression of the spectra with time.

To better understand the gelation mechanism, UV-vis spec-troscopy is utilized to track the generation and consumption of the quinone. First, the UV spectra of Gel-cat under slightly acidic condition (pH=6) (FIG. 3) since the quinone is highly reactive and unstable at basic pH25 was evaluated. Upon NaIO$_4$ addition (NaIO$_4$:cat=1:1), the quinone peak (at 395 nm2,3) appears immediately and surges slightly in the following 30 minutes. Meanwhile, two new peaks around 281 nm and 484 nm originated from the dicatechol formation2,3,26 can be observed ((a) and (b), FIG. 2). At pH 7.4, the dicatechol peaks are more prominent due to the faster reaction at this pH. As expected, the existence of PEG-NH$_2$ (as negative control) will not alter the process of quinone and the dicatechol formation ((c), FIG. 2). In contrast, the existence of PEG-NCSN rapidly consumes the quinones and substantially suppresses the formation of dicatechol structures. As shown in FIG. 4, upon the addition of NaIO4, the quinone peak appears immediately and then decreases in the following 10 min. The dicatechol peaks can hardly be observed for up to 45 min. Meanwhile, a new peak at around 287 nm appears, which is believed to be the absorbance of thiourea substituted catechol.[27,28] Under more acidic conditions (pH 4.0 or 2.0), the rapid consumption of quinone by the reducing thiourea becomes more significant. The rapid quinone consumption indicates the effective thiourea-quinone coupling that restores the quinone to catechol as shown in the reactions between small molecules[20]. Such effective coupling is possibly owing to the low pKa and excellent nucleophilicity of the thiourea group, leading to the fast formation of the hydrogels and the preservation of an appreciable amount of catechols.

Figure 2:
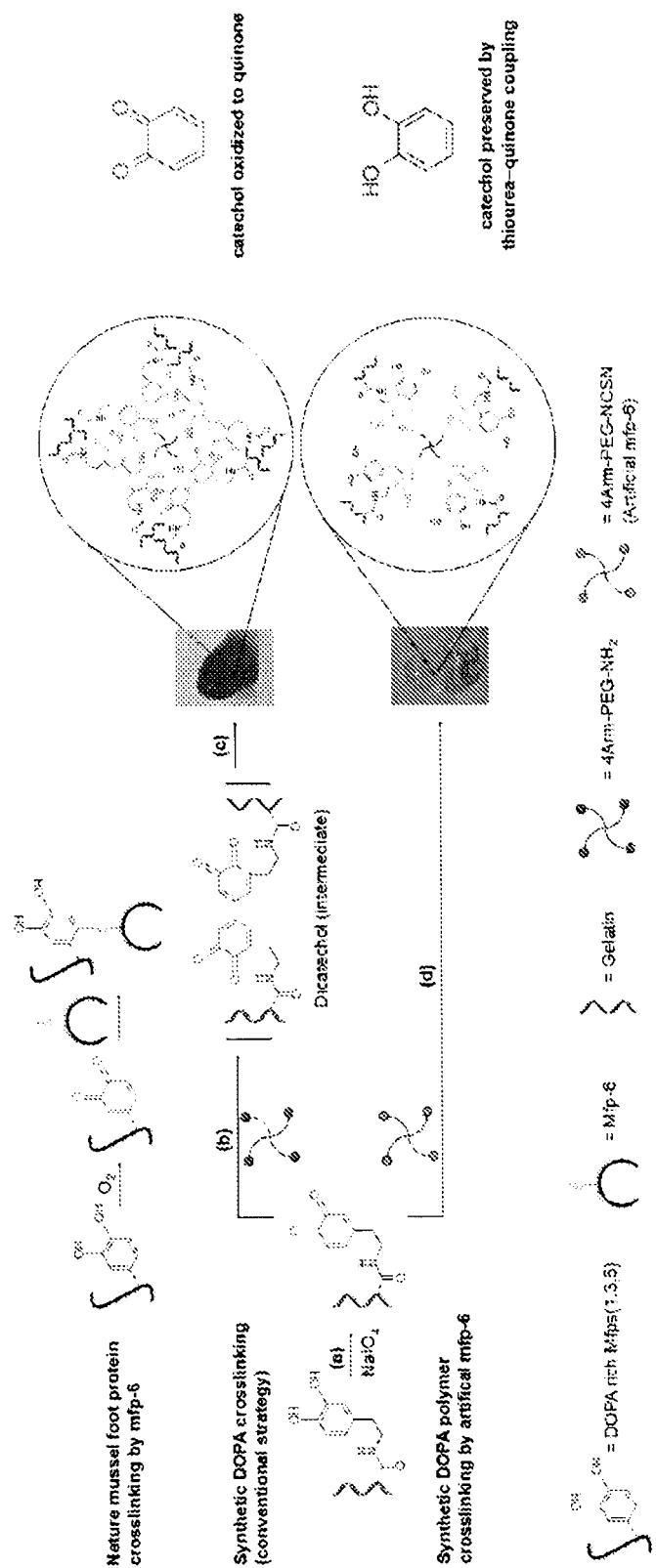
FIG. 2 shows the proposed reaction pathways in nature and biosynthetic polymers (with/without artificial mfp-6) (a) Catechol oxidized to quinone (b) quinone further reacts with unoxidized catechol to form dicatechol crosslinker (c) dicatechol further reacts with PEG-NH$_2$. (d) quinone fast reacts with thiourea modified PEG-NCSN.

This gelation mechanism of Gel-NCSN-cat is similar to that of the natural mussel proteins, where mfp-6 plays a key role in diminishing the oxidation of catechol and preventing the loss of adhesive properties of mussel feet.[13-15,17,29] Therefore, it is believed that the thiourea-functionalized polymers can mimic mfp-6 for the restoration of the catechol and formation of excellent hydrogel adhesives ((d), FIG. 2).

Example 8

Lap-Shear Measurements

Figure 6A:
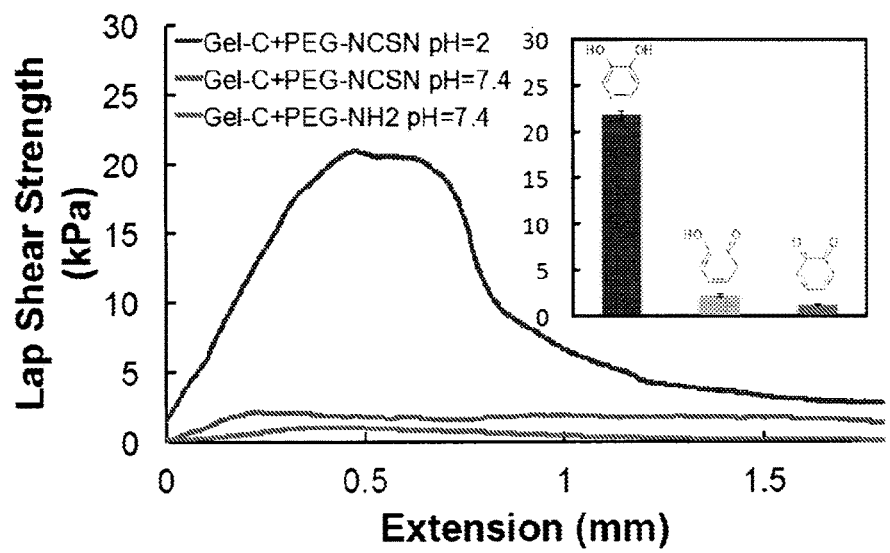
FIGS. 6A and 6B show the lap-shear adhesion strength of the catechol-conjugated polymers.

To examine the adhesiveness of the hydrogels, two Lap-shear measurements were performed. For the hydrogel preparation, we use Gel-cat (10%) as the artificial DOPA-rich mfps (mfp-1,3,5) and PEG-NCSN (4%) as the artificial mfp-6 (without DOPA). Additionally, we studied the combination of Gel-cat and PEG-NH$_2$ (4%) as the negative control. All the samples are lap shear-tested to failure on a universal testing machine with the speed of 1 mm/min under the ambient condition. Successive adhesive strength measurements are conducted for at least five times to investigate the recovery of the adhesion properties of the hydrogels.[4] All the testing hydrogels are immersed in DI water for 3 before the next testing. Then the lap-shear strength is measured in the same manner. Notably, the highest adhesion strength can be achieved by the PEG-NCSN (artificial mfp-6) crosslinked Gel-cat hydrogels at the acidic pH (pH=2.0, ~21 kPa, FIG. 6A). At pH=7.4, the lap-shear strength declines to only 2 kPa. This may be caused by the compromised reducing power of thiourea under basic conditions. Nevertheless, the adhesive strength of the hydrogels crosslinked by the PEG-NCSN is still higher than that of the PEG-NH$_2$ crosslinked hydrogels (~1 KPa), suggesting that the thiourea-mediated crosslinking mechanism still overrides the quinone-mediated mechanism at pH7.4.

Example 9

Recovery of Adhesion

Figure 6B:
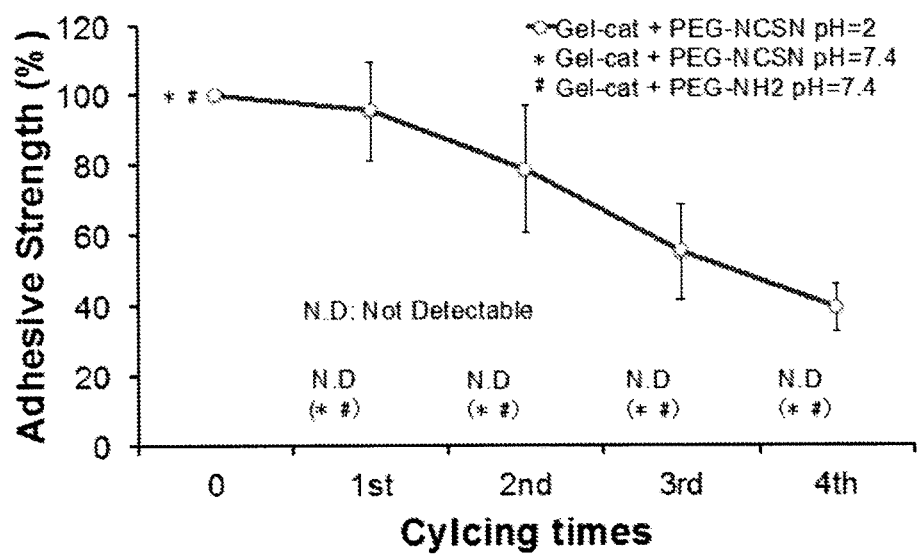
Figure 7:
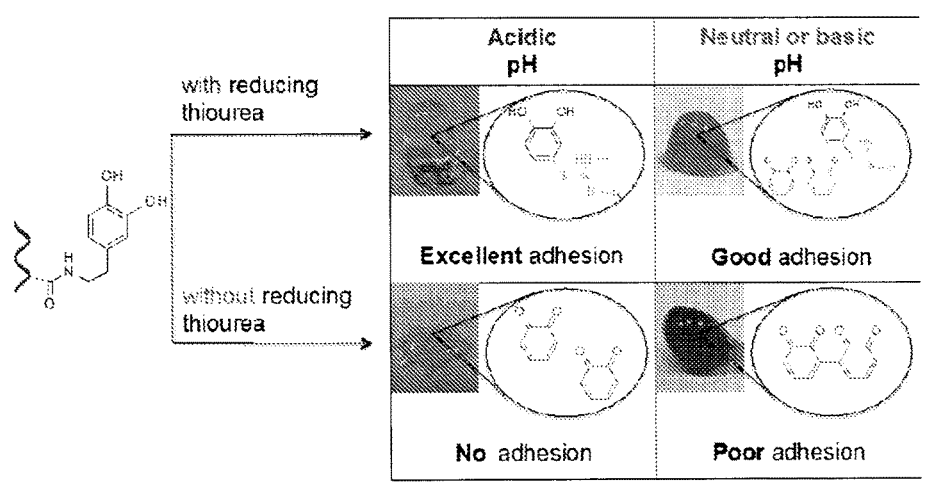
FIG. 7 shows the relative adhesion of catechol-conjugated polymers with and without thiourea present and at different pH ranges.

PEG-NCSN (artificial mfp-6) crosslinked Gel-cat hydrogels can partially recover the adhesion after being sheared to failure at acidic pH. Remarkably, the first recovery is nearly 100% (FIG. 6B), and the PEG-NCSN hydrogels can still recover 40% of the initial adhesion strength after 5 lap-shear measurements. However, such self-recovery of adhesion is diminished with increasing pH (pH7.4). In contrast, the PEG-NH$_2$ crosslinked hydrogels show no recovery of adhesion properties after the first lap-shear measurement regardless of the pH. Such difference indicates that the adhesion of thiourea-based hydrogels is mediated by reversible hydrogen-bonding between the preserved catechols and the surfaces.

In summary, a novel strategy to improve the adhesion properties of catechol-conjugated gelatin hydrogels is described. For the first time, thiourea-quinone coupling for the polymer crosslinking and hydrogel preparation was employed. Such effective coupling reaction and the reducing power of thiourea at acidic pH significantly improve the hydrogel adhesiveness. The present invention can also be applied in many other areas of DOPA research (such as surface coating) and polymer chemistry (such as click chemistry and protein conjugation).

All patents, patent applications, and other publications, including GenBank Accession Numbers, cited in this application are incorporated by reference in the entirety for all purposes.

REFERENCES (1) Hong, S.; Yang, K.; Kang, B.; Lee, C.; Song, I. T.; Byun, E.; Park, K. I.; Cho, S. W.; Lee, H. Advanced Functional Materials 2013, 23, 1774.
(2) Cencer, M.; Liu, Y.; Winter, A.; Murley, M.; Meng, H.; Lee, B. P. Biomacromolecules 2014, 15, 2861.
(3) Lee, B. P.; Dalsin, J. L.; Messersmith, P. B. Biomacromolecules 2002, 3, 1038.
(4) Kim, B. J.; Oh, D. X.; Kim, S.; Seo, J. H.; Hwang, D. S.; Masic, A.; Han, D. K.; Cha, H. J. Biomacromolecules 2014, 15, 1579.
(5) Danner, E. W.; Kan, Y.; Hammer, M. U.; Israelachvili, J. N.; Waite, J. H. Biochemistry 2012, 51, 6511.
(6) Anderson, T. H.; Yu, J.; Estrada, A.; Hammer, M. U.; Waite, J. H.; Israelachvili, J. N. Advanced functional materials 2010, 20, 4196.
(7) Kan, Y.; Danner, E. W.; Israelachvili, J. N.; Chen, Y.; Waite, J. H. 2014.
(8) Wei, W.; Yu, J.; Broomell, C.; Israelachvili, J. N.; Waite, J. H. Journal of the American Chemical Society 2012, 135, 377.
(9) Yu, J.; Wei, W.; Danner, E.; Israelachvili, J. N.; Waite, J. H. Advanced Materials 2011, 23, 2362.
(10) Lee, H.; Scherer, N. F.; Messersmith, P. B. Proceedings of the National Academy of Sciences 2006, 103, 12999.
(11) Hwang, D. S.; Harrington, M. J.; Lu, Q.; Masic, A.; Zeng, H.; Waite, J. H. Journal of materials chemistry 2012, 22, 15530.
(12) Yu, J.; Wei, W.; Menyo, M. S.; Masic, A.; Waite, J. H.; Israelachvili, J. N. Biomacromolecules 2013, 14, 1072.
(13) Yu, J.; Wei, W.; Danner, E.; Ashley, R. K.; Israelachvili, J. N.; Waite, J. H. Nature chemical biology 2011, 7, 588.
(14) Nicklisch, S. C. T.; Waite, J. H. Biofouling 2012, 28, 865.
(15) Zhao, H.; Waite, J. H. Journal of Biological Chemistry 2006, 281, 26150.
(16) Martinez Rodriguez, N. R.; Das, S.; Kaufman, Y.; Israela-chvili, J. N.; Waite, J. H. Biofouling 2015, 31, 221.
(17) Nicklisch, S. C. T.; Das, S.; Martinez Rodriguez, N. R.; Waite, J. H.; Israelachvili, J. N. Biotechnology progress 2013, 29, 1587.
(18) Harris, T. K.; Turner, G. J. IUBMB life 2002, 53, 85.
(19) Schiessl, W. C.; Summa, N. K.; Weber, C. F.; Gubo, S.; Dücker-Benfer, C.; Puchta, R.; van Eikema Hommes, N. J. R.; van Eldik, R. Zeitschrift für anorganische und allgemeine Chemie 2005, 631, 2812.
(20) Abdel-Mohsen, H. T.; Conrad, J. r.; Beifuss, U. The Journal of organic chemistry 2013, 78, 7986.
(21) Wang, X.; Li, Z.; Shi, J.; Wu, H.; Jiang, Z.; Zhang, W.; Song, X.; Ai, Q. ACS Catalysis 2014, 4, 962.
(22) Medintz, I. L.; Stewart, M. H.; Trammell, S. A.; Susumu, K.; Delehanty, J. B.; Mei, B. C.; Melinger, J. S.; Blanco-Canosa, J. B.; Dawson, P. E.; Mattoussi, H. Nature materials 2010, 9, 676.
(23) Ji, X.; Palui, G.; Avellini, T.; Na, H. B.; Yi, C.; Knappen-berger Jr, K. L.; Mattoussi, H. Journal of the American Chemical Society 2012, 134, 6006.
(24) Liu, Y.; Meng, H.; Konst, S.; Sarmiento, R.; Rajachar, R.; Lee, B. P. ACS applied materials & interfaces 2014, 6, 16982.
(25) Xu, H.; Nishida, J.; Ma, W.; Wu, H.; Kobayashi, M.; Otsu-ka, H.; Takahara, A. ACS Macro Letters 2012, 1, 457.
(26) Graham, D. G.; Jeffs, P. W. Journal of Biological Chemistry 1977, 252, 5729.
(27) Land, E. J.; Perona, A.; Ramsden, C. A.; Riley, P. A. Organic & biomolecular chemistry 2009, 7, 944.
(28) Borovansky, J.; Edge, R.; Land, E. J.; Navaratnam, S.; Pavel, S.; Ramsden, C. A.; Riley, P. A.; Smit, N. P. M. Pigment cell research 2006, 19, 170.
(29) Zhao, H.; Waite, J. H. Biochemistry 2005, 44, 15915.

What is claimed is:

1. A method of preparing a multi-compound chemical structure using a catechol-functionalized compound and a thiourea-functionalized di-compound polymer, comprising the steps of:
   (a) oxidizing the catechol-functionalized compound in the presence of an oxidizing agent to form the corresponding oxidized catechol-functionalized compound; and
   (b) conjugating the oxidized catechol-functionalized compound with the thiourea-functionalized di-compound polymer to form a catechol-conjugated tri-compound polymer.

2. The method of claim 1, further comprising, subsequent to step (b):
   (c) under oxidizing conditions, conjugating at least one thiol-functionalized compound to the catechol-conjugated tri-compound polymer to form a multi-compound chemical structure.

3. The method of claim 2, wherein two different thiol-functionalized compounds are conjugated to the catechol-conjugated tri-compound polymer in step (c) to form a multi-compound chemical structure.

4. The method of claim 1, further comprising, prior to step (a), attaching a catechol molecule to a compound to form the catechol-functionalized compound.

5. The method of claim 2, further comprising, prior to step (a), attaching a catechol molecule to a compound to form the catechol-functionalized compound.

6. The method of claim 1, further comprising, prior to step (a), reacting a compound having an amine group with another compound having an isothiocyanate group in an amine-isothiocyante reaction to form a thiourea-functionalized di-compound polymer.

7. The method of claim 2, further comprising, prior to step (a), reacting a compound having an amine group with another compound having an isothiocyanate group in an amine-isothiocyante reaction to form a thiourea-functionalized di-compound polymer.

8. The method of claim 1, wherein step (b) is conducted in the presence of an organic solvent or an aqueous solvent.

9. The method of claim 1, wherein step (b) is conducted at a pH of about 1 to about 14, or about 2.0.

10. The method of claim 1, wherein the oxidizing agent is selected from the group consisting of $NaIO_4$, $KIO_4$, $NaMnO_4$, $KMnO_4$, $Na_2Cr_2O_7$, $K_2Cr_2O_7$, $CrO_3$, and Mushroom Tyrosinase.

11. The method of claim 1, further comprising conducting said step (b) conjugation at oxidizing agent to catechol-functionalized compound ratio between 0.5 and 9999.

12. The method of claim 1, wherein the steps are represented by scheme 1:

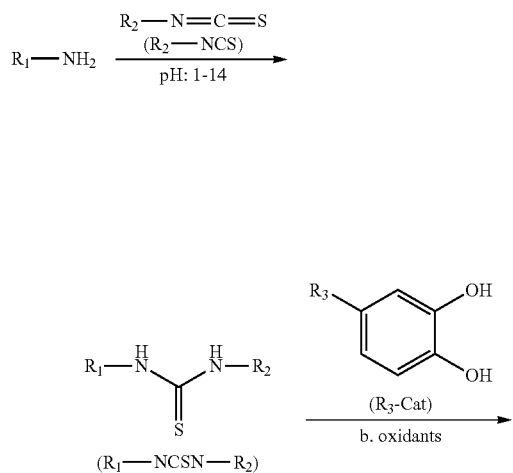

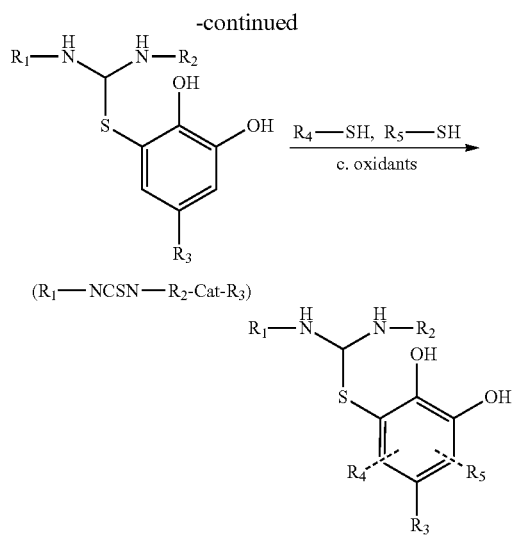

wherein $R_1$, $R_2$, $R_3$, $R_4$, and $R_5$ are independently the same or different from each other, each of $R_1$, $R_2$, $R_3$, $R_4$, and $R_5$ being independently a small molecule, a polymer, a macromolecule, a nanoparticle, or a surface of solid material.

* * * * *